(12) United States Patent
Fine

(10) Patent No.: US 9,884,010 B2
(45) Date of Patent: Feb. 6, 2018

(54) DENTAL HYGIENE SYSTEMS

(71) Applicant: Kenneth Davin Fine, Dallas, TX (US)

(72) Inventor: Kenneth Davin Fine, Dallas, TX (US)

( * ) Notice: Subject to any disclaimer, the term of this patent is extended or adjusted under 35 U.S.C. 154(b) by 0 days.

(21) Appl. No.: 15/096,489

(22) Filed: Apr. 12, 2016

(65) Prior Publication Data
US 2016/0324765 A1  Nov. 10, 2016

Related U.S. Application Data

(60) Provisional application No. 62/147,036, filed on Apr. 14, 2015.

(51) Int. Cl.
| | | |
|---|---|---|
| *A61K 8/99* | (2017.01) | |
| *A61K 8/58* | (2006.01) | |
| *A61K 8/02* | (2006.01) | |
| *A61Q 11/00* | (2006.01) | |
| *A61K 8/19* | (2006.01) | |
| *A61K 8/21* | (2006.01) | |

(52) U.S. Cl.
CPC ................ *A61K 8/99* (2013.01); *A61K 8/022* (2013.01); *A61K 8/0225* (2013.01); *A61K 8/0241* (2013.01); *A61K 8/19* (2013.01); *A61K 8/21* (2013.01); *A61Q 11/00* (2013.01); *A61K 2800/87* (2013.01)

(58) Field of Classification Search
USPC .................... 424/48, 52, 54, 57, 474
See application file for complete search history.

(56) References Cited

U.S. PATENT DOCUMENTS

| | | | | |
|---|---|---|---|---|
| 2,265,102 | A * | 12/1941 | Cressler | A46B 9/005 15/167.1 |
| 3,655,867 | A * | 4/1972 | Schoernig | A61K 8/21 424/52 |
| 6,379,651 | B1 * | 4/2002 | Athanikar | A61K 8/19 424/440 |
| 2014/0065218 | A1 * | 3/2014 | Lang | A61K 35/744 424/474 |

* cited by examiner

*Primary Examiner* — Walter Webb
(74) *Attorney, Agent, or Firm* — Ferguson Braswell Fraser Kubasta PC; Elizabeth Philip Dahm; Kelly J. Kubasta

(57) ABSTRACT

In various implementations, a dental hygiene system may include a dental powder. The dental powder may include one or more compounds comprising calcium and/or magnesium. The dental powder may include one or more probiotics, in some implementations. The dental hygiene system (e.g., dental powder) may include bismuth subsalicylate. The dental hygiene system may include an applicator and the dental powder may be applied to the applicator. A user may use the dental hygiene system to improve a user's dental hygiene.

11 Claims, 1 Drawing Sheet

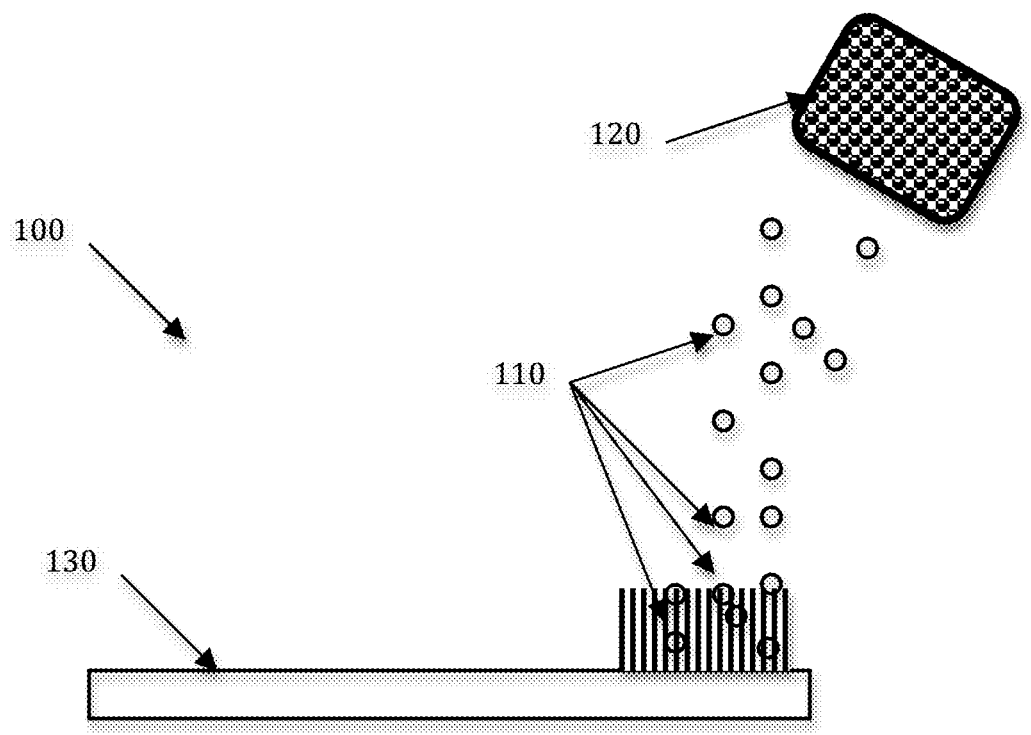

DENTAL HYGIENE SYSTEMS

CROSS-REFERENCE TO RELATED APPLICATION

This application claims the benefit of U.S. Provisional Patent Application No. 62/147,036, entitled "DENTAL HYGIENE SYSTEMS," filed on Apr. 14, 2015, which is hereby incorporated by reference for all purposes.

TECHNICAL FIELD

The present invention relates to dental hygiene systems.

BACKGROUND

Poor dental hygiene can cause tooth decay, gum disease, and/or bad breath. Local formation of acidic organic compounds by cariogenic bacteria has been determined to be an important mechanism of dental cavity formation by acid-dissolution of tooth structure. In addition, consumption of many pigmented foods can cause staining of teeth. Consequently, people use toothpastes, sonic toothbrushes, mouthwashes, bleaching agents, and other dental products seeking better dental hygiene and whiter teeth. However, many products contain undesirable compounds that may be harmful to your health (e.g., antibiotics such as triclosan, harsh bleaching agents that can erode enamel) or compounds that a person may not desire to use (e.g., alcohol).

SUMMARY

In various implementations, a dental hygiene system may include a dental powder. The dental hygiene system may whiten teeth, reduce cavities by reducing the amount of harmful bacteria present in a mouth, improve mouth health, and/or improve user health, in some implementations. The dental powder may include an antacid powder. In some implementations, the dental powder may include one or more basic mineral salts that include calcium carbonate, magnesium carbonate, and/or other similar compounds. For example, the dental powder may include dolomite, a natural occurring mineral containing these salts, and/or predetermined combinations of calcium carbonate and/or magnesium carbonate (e.g., isolated calcium carbonate and/or isolated magnesium carbonate). The dental powder may include one or more probiotics, in some implementations. The dental powder may be applied to (e.g., brushed onto) at least a portion of the teeth and/or at least a portion of the gums of a user's mouth. In some implementations, the dental powder may be administered by mixing the dental powder in a hydrating solution (e.g., water) to allow a user to swish and/or swallow the dental powder solution. The dental powder solution administration may provide an antacid mechanism (e.g., in the region of the teeth and/or gums) and/or provide nutritional supplementation (e.g., calcium and/or magnesium).

In various implementations, a dental hygiene system may include a dental powder. The dental powder may include one or more probiotics and a first compound, which includes calcium.

Implementations may include one or more of the following features. The dental powder may include a second compound, and wherein the second compound comprises magnesium. The first compound may include magnesium. The dental powder may include a second compound, which includes fluoride. In some implementations, the dental powder may include zinc citrate, potassium nitrate, strontium chloride, pyrophosphate, silica abrasive, aluminum oxide, phosphate salts, foaming agent, xylitol, flavoring agent, and/or color additive. In some implementations, the dental powder may be granular. The average particle size of the dental powder may be between approximately 10 microns and approximately 300 microns. One or more of the probiotic may include a *Lactobacillus* species and/or a non-pathogenic Streptococci species. The dental powder may include a weight percentage of fat less than 5% of total dental powder weight, a weight percentage of protein less than 5% of total dental powder weight, and/or a weight percentage of carbohydrate less than 5% of total dental powder weight. The dental hygiene system may include an applicator. The dental powder may be applied to the applicator, and the applicator may apply the dental powder to one or more of a user's teeth. The dental hygiene system may include a hydrating agent.

In various implementations, a dental hygiene system may include a dental powder. The dental powder may include a first composition. The first composition may include calcium and magnesium. The ratio of calcium (e.g., isolated calcium) to magnesium (e.g., isolated magnesium) in the first composition may be approximately 1:1 to approximately 2:1. The first composition may have a basic pH. The dental powder may be applied to one or more of a user's teeth during application.

Implementations may include one or more of the following features. The dental hygiene system may include a solid bar that includes the dental powder. The dental powder may be distributed in the bar such that at least a portion of the dental powder may contact a user's tooth when the bar is rubbed against the user's tooth. The dental powder may include one or more second compositions. The second composition(s) may include zinc citrate, potassium nitrate, strontium chloride, pyrophosphates, silica abrasive, aluminum oxide, phosphate salts, foaming agent, xylitol, flavoring agent, and/or color additive. The dental powder may be granular. The average particle size of the dental powder may be approximately 10 microns to approximately 100 microns. The dental powder and/or the hydrating agent may include bismuth subsalicylate.

In various implementations, a dental hygiene system may include a dental powder comprising one or more probiotics; an applicator; and a hydrating agent.

Implementations may include one or more of the following features. The dental powder may be consumable (e.g., by a user). The hydrating agent may at least partially revive one or more of the probiotics in the dental powder. The dental powder may include granules (e.g., the probiotic(s), first composition, second composition, and/or other compositions may be granular). The granules may at least partially abrade one or more surfaces of a tooth during application of the dental powder to a user's teeth. The dental hygiene system may include a paste, and the paste may include the dental powder. The probiotic(s) may promote health flora in a user's mouth after application of the dental hygiene system. The dental powder and/or the hydrating agent may include bismuth subsalicylate.

In various implementations, the dental hygiene system may include administration of bismuth subsalicylate to treat periodontitis (e.g., to reduce inflammation, bacteria growth, and/or bone loss associated with periodontitis). The dental hygiene system may include a dental powder and/or hydrating agent that includes bismuth subsalicylate.

Implementations may include one or more of the following features. The dental powder may include bismuth subsalicylate. The dental powder may include a first composition that includes calcium and/or magnesium; one or more probiotics; and/or third compounds. The dental powder may be granular. The bismuth subsalicylate may be administered via a hydrating agent (e.g., a mouth wash) prior to and/or before administration of a dental powder that includes a first composition that includes calcium and/or magnesium; probiotics; and/or third composition(s).

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 illustrates an implementation of dental hygiene system.

Like reference symbols in the various drawings indicate like elements.

DETAILED DESCRIPTION

In various implementations, a dental hygiene system may be utilized for dental hygiene. The dental hygiene system may include a dental powder. The dental hygiene system may include an applicator and the dental powder may be applied to the applicator (e.g., from a container) to use the dental hygiene system. The applicator may be used to apply the dental powder to at least a portion (e.g., a portion or all) of a user's mouth (e.g., teeth and/or gums). In some implementations, using the dental hygiene system may improve dental hygiene, dental health (e.g., by inhibiting gingivitis, treating periodontitis, and/or inhibiting periodontitis), whiteness of the teeth, bad breath (e.g., due to halitosis), and/or other dental properties (e.g., when compared to not using the dental hygiene system).

In various implementations, the dental hygiene system may include a dental powder. The dental powder may include an antacid powder, in some implementations. The dental powder may have a basic pH. For example, the dental powder may have a pH of greater than 7 and less than 11. By utilizing a basic dental powder (e.g., a dental powder with a basic pH), acidity in a user's mouth may be reduced. For example, at least a portion of the acidic compounds in a user's mouth maybe neutralized by interaction with the basic dental powder (e.g., brushing, swishing a dental powder solution, or otherwise applying). Reducing the acidity of a user's mouth may decrease cavity formation, inhibit at least a portion of the less healthful bacteria growth (e.g., that cause cavities and/or bad breath), reduce acid erosion of enamel and/or otherwise improve dental hygiene (e.g., when compared with not using the dental hygiene system).

In various implementations, the dental powder may include one or more compounds that include magnesium and/or calcium. The calcium may improve dental health (e.g., increase tooth strength and/or decrease tooth decay). The magnesium may decrease tooth decay, in some implementations. The dental powder may include a carbonate (e.g., magnesium carbonate, calcium carbonate, and/or calcium magnesium carbonate). The dental powder may include a probiotic. In some implementations, the dental powder may include a first compound that includes both calcium and magnesium. For example, the dental powder may include dolomite. The dental powder may include a predetermined amount of calcium and/or magnesium. For example, a dental powder may include a predetermined ratio (e.g., approximately 1:approximately 1, approximately 2:approximately 1, and/or any other appropriate ratio) of isolated calcium and isolated magnesium. For example, the dental powder may include a first compound with a stoichiometric ratio of approximately 1:1 to approximately 2:1 of calcium to magnesium. In some implementations, the dental powder may include a probiotic.

In some implementations, the dental powder may include a combination (e.g., composition) of one or more types of compounds. For example, the dental powder may include one or more first compounds (e.g., a first composition of one or more first compounds), one or more second compounds (e.g., a second composition of one or more second compounds), and/or one or more other compounds (e.g., other compositions of one or more other compounds). The first compound(s) may include one or more compounds that include calcium and/or magnesium.

The second compound(s) may include a calcium compound, a fluoride compound, a carbonate compound and/or a probiotic. For example, the dental powder may include dolomite, which includes calcium and magnesium, and calcium carbonate. The dental powder may include dolomite and a fluoride salt (e.g., sodium fluoride, stannous fluoride).

In some implementations, the dental powder may include one or more third compounds such as zinc citrate, potassium nitrate, strontium chloride, pryrophosphates, silica abrasives (e.g., dehydrated silica gels), aluminum oxides, phosphate salts, glycerin, foaming agents (e.g., sodium lauryl sulfate, sodium N-lauryl sarcosinate), xylitol, flavoring agents, color additives, western medicinal herbs, eastern medicinal herbs, and/or any other appropriate compound. For example, one or more herbs (e.g., myrrh, chaparral, parsley oil, *echinacea*, goldenseal, xylitol, gotu kola, kola, other appropriate herbs, and/or combinations thereof) may be included in the third compounds to reduce odor (e.g., in the mouth), improve tissue health (e.g., when compared to not using the composition), improve mouth health (e.g., when compared to not using the composition) and/or provide antiseptic, anti-inflammatory, tissue healing, antibacterial, and/or other appropriate qualities to the dental powder. The quantity of the herbs (e.g., myrrh, chaparral, parsley oil, *echinacea*, goldenseal, xylitol, gotu kola, kola, other appropriate herbs, and/or combinations thereof) administered may be an effective amount for mouth health. The quantity of these herbs administered may not exceed maximum daily and/or yearly amounts (e.g., as provided by the US FDA or other regulatory agency).

In various implementations, the dental powder may include one or more first compounds, one or more second compounds, and/or one or more third compounds. For example, the dental powder may include dolomite and a probiotic. The dental powder may include dolomite, a probiotic, and a fluoride compound, in some implementations. The dental powder may include a probiotic and a flavoring agent, in some implementations.

In some implementations, the dental powder may include at least one granular compound. Utilizing a granular dental powder that includes calcium and/or magnesium may increase tooth whiteness (e.g., when compared with not using the dental powder). For example, the dental powder may include a granular first composition, granular second composition, and/or other granular compositions. The dental powder may be a mixture of the granular compositions. The dental powder may include mixture of granular and finer particles. In some implementations, the one or more compositions of the dental powder may be processed (e.g., processed to form particles, mixed with an inert compound such as a binder to form granules, and/or any other appropriate process) to form a granular dental powder. The granular dental powder may include a compound with a granular size (e.g., average granular size) large enough to allow the granules to abrade at least a portion of a surface of a tooth and/or a granular size small enough to facilitate use by a user (e.g., if the granule size is too large then it may be difficult to apply to an applicator and a tooth, if the granule size is too large it may not provide enough surface area to abrade the surface of a tooth, and/or if the granule size is too small the granule may fully dissolve in the presence of saliva). The granular dental powder may have a hardness that allows the dental powder to abrade at least a portion of a surface of a tooth (e.g., to remove stains) during application without substantially damaging the enamel of the tooth. The granular dental powder may include at least one compound with an average particle size between approximately 300 microns and approximately 10 microns and/or any other appropriate particle size range. In some implementations, the granules in the dental powder may have an average particle size less than approximately 74 microns. In some implementations, the granules in the dental powder may have an average particle size of approximately 10 microns to approximately 74 microns. For example, the dental powder may include granular dolomite. The granular dolomite may have an average particle size less than approximately 44 microns. In some implementations, the granular dental powder, such as granular dolomite, may have an average particle size of 5 microns to approximately 44 microns. The granules in the dental powder may abrade and/or at least partially remove stains from at least a portion of a surface of a tooth.

In some implementations, the particles (e.g., dolomite) in the dental powder may at least partially dissolve when in contact with acidic conditions in the mouth since the particles (e.g., dolomite) may be basic. The abrasiveness and/or particle size of the particles (e.g., dolomite) on the tooth may then be decreased to inhibit overabrasion of the enamel of a tooth, in some implementations.

In some implementations, the dental powder may have a granule size (e.g., average particle size) to at least partially dissolve and/or mix with a hydrating agent for administration in a user's mouth. For example, the dental powder may be mixed with a hydrating agent, such as water, to form a dental powder solution. The granule size of the dental powder may be selected to that the dental powder may temporarily remain suspended in the solution (e.g., the dental powder may not immediately sink to the bottom of a cup of dental powder solution), dissolve, and/or otherwise facilitate the application of the dental powder solution in a mouth. For example, the dental powder may not fully dissolve in the hydrating agent to allow the dental powder to abrade a surface of a tooth during administration of the dental powder. In some implementations, the dental powder may dissolve in the hydrating agent and may not at least partially abrade a surface of the enamel of the tooth (e.g., when utilizing a dental powder with probiotics, bismuth sub salicylate, calcium, fluoride, etc.).

In some implementations, the particles (e.g., dolomite) in the dental powder may at least partially dissolve in the presence of a hydrating agent applied to the dental powder. The abrasiveness of the particles of the dental powder on the tooth may be decreased at least partially dissolving the particles. In some implementations, by at least partially dissolving the particles in the dental powder in the hydrating agent, the acidity of the mouth may be decreased (e.g., when compared not dissolving the dental powder).

In some implementations, the dental powder may include a probiotic. The probiotic may promote the growth of healthful bacteria (e.g., probiotic bacteria) over less healthful bacteria (e.g., that cause cavities and/or bad breath) in a user's mouth. For example, the probiotics in the dental powder may include live or dormant healthful bacteria that when present in internal body cavities of the body (e.g., intestinal tract, oral cavity, and/or vagina) have been proven to overcome the growth of less healthful bacteria (e.g., anaerobic bacteria). Since the type of bacteria that metabolize saliva, mucus, and foodstuffs into odiferous aromatic compounds and/or damage a tooth may include the same or similar types of less healthful bacteria, the application of a probiotic dental powder may inhibit odor and/or cavities by allowing one of more of the bacteria of the probiotic bacteria to overcome the growth of the less healthful bacteria.

In some implementations, the probiotics in a dental powder may promote the growth of bacteria in a user's mouth that promotes dental hygiene. For example, by applying the dental powder to at least a portion of the mouth (e.g., gums and/or teeth), the user may deposit at least a portion of the probiotics from the dental powder onto the teeth and/or gums. In some implementations, at least a portion of a desiccated dormant probiotic may be revived by rehydration from the saliva present in the user's mouth. The probiotics deposited in the mouth may grow (e.g., binary fission). As the probiotics in the mouth grow, other bacteria present in the area may exist in lower magnitudes and/or die (e.g., the colony may enter the death phase). When the previously existing bacteria are in lower magnitudes and/or die, dental hygiene (e.g., the probability of cavities, bad breath, gingivitis, and/or periodontitis) may be increased (e.g., when compared with dental hygiene without application of the dental powder).

In some implementations, the probiotics utilized in the dental powder may be selected from a group of bacteria based on odor inhibiting criteria, cavity fighting criteria, gingivitis-preventing criteria, and/or periodontitis-preventing criteria. The bacteria selected may not produce common predetermined odor causing compounds in high levels (e.g., greater than 20%).

In various implementations, the probiotic may include one or more predetermined strains of bacteria (e.g. *Lactobacillus* species, non-pathogenic Streptococci). In some implementations, the organisms (e.g., bacteria) in the probiotic may be live, dried, and/or combinations thereof. The organisms in the probiotic may be similar or identical to one or more of the bacteria used in intestinal probiotic preparations, such as the previously mentioned *Lactobacillus* and Streptococci species. In some implementations, the organism(s) selected for inclusion in the dental powder may be selected to be similar to that of bacteria present in a healthy mouth bacterial flora.

In some implementations, the use of probiotic dental powder may improve and/or maintain healthy intestinal flora of a user since at least a portion of the dental powder may be consumed by the user during use. For example, when the dental powder is applied to the teeth of a user using an applicator, at least a portion of the dental powder may mix with saliva in the mouth and may be consumed by the user. In some implementations, the dental powder may be applied to a user by mixing the dental powder with water to create a dental powder solution. The dental powder solution may be gargled, swished, and/or otherwise moved around in a users mouth. At least a portion of the dental powder solution may be consumed by the user, as the user swishes the dental powder solution. In some implementations, the dental powder solution may be consumed by the user after swishing the dental powder solution in the users mouth.

In some implementations, the dental powder may include a dried probiotic (e.g., freeze dried). The dried probiotic may include dried bacteria. The dried bacteria may include dormant or inert bacteria. By utilizing dried probiotics, the shelf life of the dental hygiene system may be increased (e.g., when compared to using live probiotic). When the probiotics are utilized in live form in the dental hygiene system, the number of probiotic organisms may decrease overtime (e.g., due to reduction in nutrients available or other reason for entry into a death phase of a colony of organisms). Thus, by utilizing dried probiotics (e.g., bacteria), the number of probiotic organisms (e.g., bacteria) in the dental hygiene system may be maintained at a higher level over time than when utilizing live probiotics.

When dried probiotics are utilized in the dental powder, at least a portion of the dried probiotics may be activated (e.g., revived) prior to and/or during application of the probiotic in a user's mouth. For example, at least a portion of the dried probiotic may be hydrated prior to application in a user's mouth (e.g., when the dental powder is applied as a dental powder solution, and/or by the application of a hydrating agent to the applicator and/or dental powder). In some implementations, at least a portion of the dried probiotic may be hydrated by the saliva present in the user's mouth. When the dried probiotic is activated (e.g., revived), the probiotic may become live probiotic. For example, when dried bacteria in a dried probiotic are activated, at least a portion of the dried bacteria may be revived (e.g., return to a live state). When applied to a user's mouth, the revived bacteria may improve and/or maintain healthy flora in the user's mouth.

In some implementations, the other compounds selected for inclusion in the dental powder may not substantially inhibit growth of the probiotic in the dental hygiene system and/or in a user. In some implementations, the other compounds may not include fat(s), protein(s), and/or carbohydrate(s) to inhibit the deodorant from fermenting, or turning putrefactive or rancid, which may generate foul odor. In some implementations, the other compounds may not include a percentage by weight of fat(s), protein(s), and/or carbohydrate(s) greater than 5% of total dental powder weight to inhibit the dental powder from turning fermenting, or turning putrefactive or rancid.

In some implementations, the dental powder may include bismuth subsalicylate (e.g., with and/or without other described compounds including calcium, magnesium, probiotics and/or third compounds). Bismuth subsalicylate may be utilized to treat and/or inhibit periodontitis. Periodontitis is an inflammatory disease that may occur when bacteria grow proximate teeth in a user's mouth. When the bismuth subsalicylate is applied (e.g., brushed) to a user's mouth or portions thereof the bismuth subsalicylate may act as an anti-inflammatory and/or exhibit antibiotic-like properties. For example, the bismuth may inhibit growth of anaerobic bacteria in the mouth that may contribute to periodontitis. The subsalicylate may act as an anti-inflammatory to treat inflammation caused by periodontitis, in some implementations.

Administration of a dental powder that includes bismuth subsalicylate may improve and/or eliminate periodontitis. In some implementations, a dental powder that includes approximately 100 mg to approximately 750 mg of bismuth subsalicylate may be administered (e.g., applied to the user's mouth). For example, the dental powder that includes bismuth subsalicylate may be administered approximately 1 to 5 times a day (e.g., after meals, upon waking, before bed, etc.). In some implementations, a dental powder that includes approximately 200 mg to approximately 500 mg of bismuth subsalicylate may be administered up to 5 times a day. The amount of bismuth subsalicylate administered may not exceed approximately 2 grams daily, in some implementations. In some implementations, a greater amount (e.g., approximately 5 grams/day) may be administered via the dental powder, when the dental powder is be applied (e.g., brushed into teeth and/or gums; swished in a similar manner to a mouth wash) but not consumed. For example, since only a small amount of bismuth subsalicylate may be adsorbed by the body and/or ingested while brushing, a greater amount than a maximum daily or yearly amount (e.g., based on US FDA guidelines) may be administered to the user. In some implementations, the user may be monitored (e.g., self and/or reportable monitoring) for tinnitus; and in the presence of tinnitus, the administration amount of bismuth subsalicylate may be reduced.

Bismuth subsalicylate may be a powder that can be processed to form a granular dental powder, and/or mixed with other compounds in the dental powder to form a granular dental powder. In some implementations, the dental powder with bismuth subsalicylate may include other forms (e.g., gel, paste, liquid, etc.). In some implementations, the bismuth subsalicylate may be provided with or without other compositions in liquid form (e.g., mouthwash) for the user to swish and/or gargle in the user' mouth.

The dental powder may include a first composition including calcium and/or magnesium; a second composition comprising probiotics; a third composition comprising bismuth subsalicylate; and/or other compositions (e.g., flavorings, etc.). For example, the dental powder may include dolomite and bismuth subsalicylate, in some implementations. In some implementations, the dental powder may include calcium, magnesium, and/or probiotics and the bismuth subsalicylate may be provided separately as part of the dental hygiene system. For example, the bismuth subsalicylate may be provided in a hydrating agent used with the dental powder. In some implementations, the bismuth subsalicylate may be provided in a mouthwash to be administered before or after the dental powder application.

The dental powder may include a first composition comprising calcium, magnesium, and/or bismuth subsalicylate. For example, the dental powder may include a granular mixture of compounds that include calcium, magnesium, and/or bismuth subsalicylate. The dental powder may be applied to the teeth and reduce inflammation and/or inhibit growth of one or more bacteria.

In some implementations, the dental powder may include one or more probiotics and bismuth subsalicylate. The dental powder may include or may not calcium and/or magnesium. A predetermined set of probiotics may be utilized that the bismuth subsalicylate does not substantially harm. For example, the bismuth subsalicylate may have antibiotic-like features that harm some types of bacteria but do not substantially harm other types of bacteria. Thus, when the dental powder includes bismuth subsalicylate and probiotics, one or more of the included probiotics may include types of bacteria that are not substantially harmed by the inclusion of bismuth subsalicylate (e.g., the probiotics may promote growth of a healthy flora in a mouth even when bismuth subsalicylate is applied to the user' mouth).

In some implementations, the dental powder may include dolomite and a probiotic. In some implementations, the dental powder may include a probiotic and not include dolomite.

In some implementations, at least a portion of the dental powder may be included in the dental hygiene system as paste (e.g., a moist substance such as a gel, cream, liquid, and/or other appropriate form). For example, dental powder may be combined with one or more hydrating agents and/or other compounds to form a paste. Providing the dental powder in paste form may ease the application of the dental powder to an applicator (e.g., of the dental hygiene system) and/or to portions of a user's mouth. By utilizing a hydrating agent to form the paste, the hydrating agent may at least partially hydrate and thus revive probiotics, if present, in the dental powder. The hydrating agent may include water, in some implementations.

In various implementations, the dental hygiene system may include an applicator. The applicator may be a toothbrush and/or other appropriate application tool to apply the dental powder (e.g., in powder form and/or via a paste that includes the dental powder) to at least a portion of the mouth of a user. For example, the application tool may include a surface that retains at least a portion of the dental powder on the applicator and allows transfer of at least a portion of the dental powder to a user's mouth during application. In some implementations, a hydrating agent (e.g., water, toothpaste, etc.) may be applied to the applicator and then the dental powder is applied to the hydrating agent (e.g., by sprinkling, dipping, etc.) on the applicator. The dental powder may stick or otherwise adhere to the hydrating agent. The application tool may include a container. The container may indicate (e.g., a level marker) a predetermined quantity for a single user of the dental powder. Or the container may be a multi-vial combination container, one containing powder and the other a hydrating substance. A hydrating agent may be added to the container prior to applying the dental powder (e.g., gargling, swishing, etc.). The container may include markings to facilitate dosage of the dental powder and/or hydrating agents. In some implementations, a user may use one or more of the user's fingers as an applicator.

In some implementations, the dental powder (e.g., directly or indirectly via a paste) may be applied to the applicator. A user may apply the dental powder to at least a portion of the teeth and/or gums of a user using the applicator. The applicator may be provided with a dental hygiene kit and/or be an applicator that a user has available (e.g., a toothbrush). The applicator may stroke (e.g., rub, rotate, scrub, and/or vibrate) the dental powder (e.g., directly or via a paste) on teeth and/or gums. A user may move the applicator and/or the applicator may at least partially automatically stroke (e.g., sonic toothbrush, rotating head toothbrush, vibrating toothbrush, etc.) the teeth and/or gums during application. By stroking the teeth during application of the dental powder, the dental powder may at least partially abrade surfaces of the teeth and/or gums to at least partially remove food particles, bacteria, plaque, and/or stains. For example, the dental powder may include first compound(s) that include calcium and magnesium, such as granular dolomite. The granules of the first compounds may at least partially abrade surfaces of at least a portion of the teeth in a user's mouth to decrease the appearance of stains on the teeth (e.g., when compared with not using the dental powder with the first compounds). The granules of the first compound may interact with at least a portion of the acids present in a user's mouth to decrease the overall and/or local acidity in the user's mouth (e.g., by neutralizing at least a portion of the acids present in the user's mouth). In some implementations, the dental powder may include a probiotic and by stroking the teeth with the dental powder, the probiotic may be dispersed in various regions of the mouth.

In some implementations, the bismuth subsalicylate in the dental powder may decrease inflammation in the mouth. By stroking the teeth during application of the dental powder with bismuth subsalicylate, the bismuth subsalicylate may decrease inflammation in the mouth.

In some implementations, a hydrating agent may be utilized to facilitate adherence of the dental powder on an applicator. The hydrating agent may include water, toothpaste, mouthwash, and/or any other appropriate hydrating agent. The hydrating agent selected for use with the dental hygiene system may be based on the type of dental powder. For example, a mouthwash that may kill at least a portion of the bacteria in the mouth may be used as a hydrating agent for a dental powder that does not include probiotics (e.g., a dolomite dental powder). Water may be used as a hydrating agent for a dental powder that includes probiotics (e.g., to revive at least a portion of the dried bacteria in the probiotics, if present). In some implementations, saliva present in the mouth of a user may at least partially revive at least a portion of the dried probiotic in a probiotic dental powder.

Applying the hydrating agent may revive organisms in the probiotic, in some implementations. By decreasing the amount of time between hydrating a dry probiotic and applying the probiotic to an area of the body, the amount of live probiotic applied to the body may be increased, in some implementations. Thus, in some implementations, the dental powder may include dried probiotics that are revived (e.g., by a user's application of a hydrating agent) prior to and/or during use.

In some implementations, a hydrating agent may be applied to the applicator (e.g., sprinkled onto an applicator, the applicator may be moistened by placing the applicator under a faucet of running water, etc.), and then dental powder may be applied to the applicator. The dental powder may be applied by sprinkling, pouring or otherwise applying the dental powder to the applicator. For example, the applicator may be at least partially hydrated (e.g., at least partially with water) prior to applying the dental powder to the applicator. In some implementations, the applicator may be hydrated and then dipped into dental powder (e.g., disposed in a container). Hydrating the applicator may increase the adherence of the dental powder to the applicator (e.g., when compared with adherence of dental powder on a dry applicator).

In some implementations, the dental powder may be in a hydrated form, such as a paste, in the dental hygiene system. The paste including the dental powder may be applied to the applicator (e.g., with or without application of a hydrating agent on the applicator). The applicator may stroke (e.g., by user action and/or automatically) the paste including the dental powder (e.g., directly or via a paste) on teeth and/or gums. If the dental powder in the paste includes granules, by stroking the teeth during application of the paste, the paste may at least partially abrade surfaces of the teeth and/or gums to at least partially remove food particles, bacteria, plaque, and/or stains. If the paste is basic and/or includes basic compounds, at least a portion of the paste may interact with at least a portion of the acids present in a user's mouth to decrease the overall and/or local acidity in the user's mouth (e.g., by neutralizing at least a portion of the acids present in the user's mouth). In some implementations, if the paste includes probiotics, the paste may facilitate the dispersal of the probiotic in various regions of the mouth.

In some implementations, the dental powder may be administered to a user via a dental powder solution. The dental powder solution may be provided to the user as a dental powder solution and/or the user may create the dental powder solution prior to use. When the dental powder solution includes probiotics, the shelf life of the probiotics may be extended by creating the dental powder solution prior to use (e.g., when compared to a pre-mixed dental powder solution provided to a user). The dental powder solution may be created by adding dental powder to a hydrating agent, such as water, mouthwash, and/or any other appropriate hydrating agent. The user may then gargle, swish, and/or otherwise move the dental powder solution around the user's mouth. By applying the dental powder solution to a user's mouth, the acidity of the mouth may be decreased (e.g., which may decrease cavities), the whiteness of the teeth may be increased (e.g., by gently abrading the surfaces of the teeth), and/or the health of the user's mouth may be otherwise improved (e.g., when compared to not administering the dental powder solution). The user may spit out the dental powder solution and/or consume the dental powder solution. Consuming at least a portion of the dental powder solution may provide an antacid properties to the gastrointestinal tract, may improve the flora of the gastrointestinal tract, and/or provide nutritional supplements (e.g., calcium and/or magnesium).

In some implementations, the dental powder may be in solid bar form. A user may rub the solid bar on teeth and/or gums in a mouth. For example, a bar of probiotic dental powder may be formed with a substrate (e.g., inert immobilization agent that could include, but would not be limited to, low moisture glycerin-like compounds or long chain fatty acid soaps with a very low moisture content, etc.) and the dental powder interspersed throughout the bar. For example, the bar may include a substrate and one or more compounds of a dental powder (e.g., dolomite, and/or a predetermined blend of isolated calcium carbonate and/or magnesium carbonate salts), and/or probiotic.

FIG. 1 illustrates an implementation of an example dental hygiene system 100. The dental hygiene system includes a dental powder 110. A dental powder 110 may be provided in a container 120. During use, a user may apply the dental powder 110 from the container 120 to an applicator 130. In some implementations, at least a portion of the dental powder 110 applied to the applicator 130 may be retained on the applicator, as illustrated. For example, prior to applying the dental powder 110 to the applicator 130, the applicator may be hydrated with a hydrating agent. When the applicator 130 is at least partially hydrated, the applicator may retain more of the applied dental powder 110 (e.g., when compared to a dry applicator). At least a portion of the dental powder 110 retained by the applicator may be transferred to a user's mouth during application of the dental powder to a user's mouth. For example, as the applicator strokes the teeth and/or gums of a user, at least a portion of the dental powder retained by the applicator may be transferred to the user's mouth.

In some implementations, the dental powder may reduce the impact of consumption of acidic foods and/or acidic compounds produced by bacteria in the mouth (e.g., when compared with the impact on a user's mouth in which the dental powder has not been applied). By utilizing a basic dental powder, acidity in a user's mouth may be reduced. In addition, in some implementations, probiotics in the dental powder may promote healthy flora in the user's mouth, which may reduce the acidic compounds (e.g., reduce the acidity and/or quantity of acidic compounds) produced by the organisms (e.g., bacteria and/or yeast) in the user's mouth.

In some implementations, a probiotic dental powder may be enclosed. Enclosing the probiotic dental powder may inhibit sunlight, moisture, and/or air exposure for the probiotic and/or increase the life of the probiotic (e.g., decrease the number of dead probiotic organisms prior to use when compared with unenclosed probiotic deodorants). The probiotic dental powder may be enclosed in a removable package. For example, a solid that includes the dental powder bar may be disposed in a removable package, such as a box with a removable lid. As another example, a probiotic dental powder may be disposed in a jar with a removable lid. In some implementations, a paste with a probiotic dental powder may be disposed in a tube (e.g., with a flip-top lid, screwing lid, open with a pump type applicator, and/or any other appropriate type of container).

In some implementations, to increase shelf-life and/or to increase the amount of live bacteria that may be applied to a mouth of a user, during use, a probiotic dental hygiene system (e.g., a dental hygiene system that includes probiotics) may be stored in a predetermined temperature range (e.g., in a refrigerator or chiller). In some implementations, the probiotic dental hygiene system may be shelf stable at room temperature in predetermined temperatures (e.g., 60-80 degrees Fahrenheit).

In some implementations, the dental powder (e.g., container including dental powder) and/or at least a portion of the dental hygiene system that includes the dental powder (e.g., toothpaste that includes dental powder) may be maintained at a first temperature range during manufacturing, sale, and/or resale (e.g., refrigerated). In some implementations, the dental powder and/or at least a portion of the dental hygiene system that includes the dental powder may be maintained at a second temperature range by a user. The second temperature range may be different or the same as the first temperature range. In some implementations, a probiotic dental powder may be refrigerated prior to sale and stored at room temperature by users. Maintaining the probiotic dental powder at the second temperature range may or may not impact the amount of live probiotic delivered to an area during application of the dental hygiene system.

The dental powder and/or dental hygiene system may be provided with a date of expiration, in some implementations. Use of the dental hygiene system that includes probiotics after the provided expiration date may deliver less than a predetermined minimum amount of probiotic to an area of application.

In some implementations, a dental hygiene system may include an effective amount of bismuth subsalicylate to treat periodontitis. For example, the dental hygiene system may administer less than approximately 2 g of bismuth subsalicylate daily. In some implementations, the dental hygiene system may topically administer (e.g., apply to the teeth and/or gums, brush onto teeth and/or gums, etc.) approximately 200 mg to approximately 500 mg per use. The dental hygiene system may be for topical application to treat periodontitis. For example, the dental hygiene system may include a dental powder with bismuth subsalicylate that is applied (e.g., topically) to the teeth and/or gums of a user's mouth. The dental powder may be granular. The dental powder may include a first composition that includes at least one of calcium and/or magnesium. The dental powder may include one or more probiotics. In some implementations, the dental powder may include one or more third compositions such as flavorings, binders, consumable solvents (e.g., to create a mouthwash solution), herbs (e.g., to promote mouth health and/or treat mouth conditions), and/or other appropriate compounds.

In some implementations, the dental hygiene system may be administered (e.g., applied by brushing, gargling, etc.) once a day or multiple times a day, as appropriate. For example, the dental hygiene system may be administered based on an individual's personalized brushing schedule, ordinary tooth brushing schedules, after meals, upon awaking, prior to sleeping, and/or other appropriate schedules. When the dental powder and/or other portions of the dental hygiene system are for consumption (e.g., after brushing or gargling), the maximum quantity of the dental hygiene system administered may be predetermined based on industry (e.g., information from journals) and/or governmental regulations (e.g., US FDA regulations). For example, the amount of magnesium may not exceed approximately 1600 mg (e.g., to inhibit gastrointestinal problems). The amount of calcium administered daily may not exceed approximately 2500 mg, in some implementations. The amount of bismuth subsalicylate administered daily may not exceed approximately 2 g, in some implementations.

In some implementations, the dental hygiene system may be single step and/or multi-step. For example, a single step dental powder may include compound(s) with calcium, magnesium, bismuth subsalicylate, probiotics, and/or third compounds (e.g., flavorings, binders, herbs, etc.). The single step dental powder may be applied to the user's mouth for administration. In some implementations, an application may be utilized to apply the single step dental powder. For example, a hydrating agent may be applied to the applicator, the dental powder may be applied to the hydrated applicator, and the dental powder may be applied to a user's mouth (e.g., by brushing the dental powder onto teeth and/or gums).

In some implementations, components of the dental hygiene system may be in the dental powder, the applicator, and/or the hydrating agent. For example, a first dental hygiene system may include a dental powder with a first compound (e.g., calcium and/or magnesium) and/or bismuth subsalicylate. A second dental powder and/or mouthwash may include probiotics, and may be used before and/or after the application of the first dental powder. In some implementations, a first dental powder and/or a mouthwash may include bismuth subsalicylate. A second dental powder may include a first compound (e.g., calcium and/or magnesium) and/or probiotics and may be applied to the user's mouth before and/or after application of the bismuth subsalicylate.

In some implementations, the dental hygiene system may be multi-step. For example, the dental hygiene system may be a kit with one or more dental powders. A user may select a dental powder for application from the kit based on the content of the dental powder and/or the health of the user's mouth. For example, a first dental powder may be associated with treating periodontitis and may include bismuth subsalicylate. The first dental powder may also include calcium, magnesium, probiotics, and/or other compounds (e.g., flavorings, binders, fluoride, herbs, and/or other appropriate compounds). A second dental powder may be associated with maintaining mouth health and include probiotics (e.g., in addition to other compounds or alone). A third dental powder may be granular and include calcium and/or magnesium to improve whiteness. Other dental powders may include other combinations as appropriate and may promote the same or other benefits. The user may select one or more of the dental powders for user together or separately. For example, a user may select the first dental powder that includes bismuth subsalicylate to treat periodontitis and then switch to a second dental powder that does not include bismuth subsalicylate once the periodontitis has improved (e.g., compared to the periodontitis prior to application of the first dental powder over a predetermined time period). In some implementations, the user may select a third dental powder that includes calcium and/or magnesium for use in the morning and a second dental powder that includes probiotics for use at other times. In some implementations, a user may select a third dental powder that includes granular calcium and/or magnesium and switch to a second dental powder that does not include granular calcium and/or magnesium once a user's teeth has become a selected level of whiteness. Other combinations may also be utilized with the dental hygiene systems, as appropriate.

Although users have been described as a human, a user may be a person or a group of people. For example, a first user may apply the dental powder to a second user's mouth. In some implementations, a first user may apply the dental powder to a second user that is a pet or other animal. For example, a first user (e.g., pet owner, veterinarian, pet groomer, etc.) may apply the dental powder, as described herein, to a dog's mouth or cat's mouth. Applying the dental powder to an animal's mouth may increase whiteness of teeth, inhibit cavities, improve flora, and/or otherwise promote hygiene, in various implementations.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a substrate" includes a combination of two or more substrates and reference to "a probiotic" includes different types and/or combinations of probiotics.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:
1. A dental hygiene system comprising:
   a dental powder, wherein the dental powder comprises a first composition, and wherein the first composition comprises:
     calcium; and
     magnesium;
     wherein the molar ratio of calcium to magnesium in the first composition is approximately 1:1 to approximately 2:1, and wherein the first composition has a basic pH;

and wherein the dental powder is applied to one or more of a user's teeth during application.

2. The dental hygiene system of claim 1 further comprising a solid bar comprising the dental powder, wherein the dental powder is distributed in the bar such that at least a portion of the dental powder may contact a user's tooth when the bar is rubbed against the user's tooth.

3. The dental hygiene system of claim 1 wherein the dental powder further comprises one or more second compositions, and wherein one or more of the second compositions comprises at least one of zinc citrate, potassium nitrate, strontium chloride, pyrophosphate, silica abrasive, aluminum oxide, phosphate salts, foaming agent, xylitol, flavoring agent, or color additive.

4. The dental hygiene system of claim 1 wherein the dental powder is granular, and wherein an average particle size of the dental powder is from approximately 10 microns to approximately 100 microns.

5. The dental hygiene system of claim 1 wherein the dental powder further comprises a probiotic.

6. The dental hygiene system of claim 1 wherein the dental powder further comprises at least one of fluoride, zinc citrate, potassium nitrate, strontium chloride, pyrophosphate, silica abrasive, aluminum oxide, phosphate salts, foaming agent, flavoring agent, color additive, myrrh, chaparral, parsley oil, *echinacea*, goldenseal, xylitol, or gotu kola.

7. The dental hygiene system of claim 1 wherein the dental powder further comprises bismuth subsalicylate.

8. The dental hygiene system of claim 1 further comprising a paste, wherein the paste includes the dental powder.

9. The dental hygiene system of claim 1 further comprising a consumable solution, and wherein the solution is mixed with the dental powder.

10. The dental hygiene system of claim 1 wherein the dental powder is applied to one or more of the user's teeth to inhibit acid erosion of enamel of the one or more user's teeth.

11. The dental hygiene system of claim 1 wherein the dental powder is applied to one or more of the user's teeth to neutralize acids in a mouth of the user.

* * * * *